United States Patent [19]

Laver

[11] Patent Number: 5,124,723
[45] Date of Patent: Jun. 23, 1992

[54] LIGHT-STABILIZED INK COMPOSITION

[75] Inventor: Hugh S. Laver, Fribourg, Switzerland

[73] Assignee: Ciba-Geigy Corporation, Ardsley, N.Y.

[21] Appl. No.: 734,013

[22] Filed: Jul. 19, 1991

Related U.S. Application Data

[62] Division of Ser. No. 569,321, Aug. 17, 1990, abandoned.

[30] Foreign Application Priority Data

Aug. 25, 1989 [CH] Switzerland .......... 3085/89
Jan. 17, 1990 [CH] Switzerland .......... 141/90

[51] Int. Cl.$^5$ .............................. G01D 9/00
[52] U.S. Cl. .......................... 346/1.1; 106/20
[58] Field of Search ............. 346/1.1; 106/20

[56] References Cited

U.S. PATENT DOCUMENTS

| | | |
|---|---|---|
| 3,282,886 | 11/1966 | Gadecki . |
| 4,256,493 | 3/1981 | Yokoyama et al. . |
| 4,780,541 | 10/1988 | Seino .................. 548/257 |
| 4,891,396 | 1/1990 | Avar et al. .......... 524/91 |
| 4,926,190 | 5/1990 | Laver ................. 346/1.1 |
| 4,929,250 | 5/1990 | Hung et al. ......... 544/180 |
| 4,964,871 | 10/1990 | Reinert et al. ..... 8/115.59 |

FOREIGN PATENT DOCUMENTS

| | | |
|---|---|---|
| 6346277 | 2/1988 | Japan . |
| 878362 | 9/1961 | United Kingdom ........ 548/257 |
| 981539 | 1/1965 | United Kingdom . |

OTHER PUBLICATIONS

Derwent Data Base 82-49174E.
Sugiyama, Masatoshi et alk., JP 57074193.
Research Disclosure 22,519 (Jan. 1983).

Primary Examiner—William R. Dixon, Jr.
Assistant Examiner—Margaret V. Einsmann
Attorney, Agent, or Firm—Luther A. R. Hall

[57] ABSTRACT 2-(2'-Hydroxyphenyl)benzotriazoles of formula I

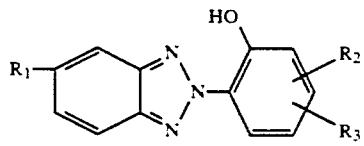

wherein $R_1$, $R_2$ and $R_3$ are as defined in claim 1, and which contain at least one —SO$_3$X group in the molecule, are suitable light stabilizing additives for aqueous ink compositions, especially for ink jet printing. Some of these compounds are novel compounds.

9 Claims, No Drawings

LIGHT-STABILIZED INK COMPOSITION

This application is a division of application Ser. No. 569,321, filed Aug. 17, 1990, now abandoned.

The present invention relates to aqueous ink compositions which contain a water-soluble derivative of a 2-(2'-hydroxyphenyl)benzotriazole. These ink compositions are particularly suitable for ink jet printing. The invention further relates to novel sulfonated 2-(2'-hydroxyphenyl)benzotriazoles.

Printing by ink jet printing is a very rapid printing method which is controlled by electrical signals. This method comprises jetting fine ink droplets through an orifice on to the recording material. The ink used is preferably an aqueous solution of a water-soluble dye. The dye will normally have a lower lightfastness than the dyestuff pigments used in conventional printing methods. The consequence is that the prints obtained have only a limited storage life when exposed to light.

The proposal has therefore already been made (U.S. Pat. No. 4,256,493) to add a water-soluble UV absorber of the sulfonated hydroxybenzophenone type to the ink. The metal salts of such compounds have also been proposed as light stabilising additives for ink jet printing inks (JP A-46277/88).

The drawback of such benzophenone derivatives and their salts is that they cause discolourations when added to specific dyes, especially black dyes.

Carboxylic acid derivatives of UV absorbers of the benzotriazole type have also been proposed in Research Disclosure 22 519 for stabilising dyes and inks. However, these derivatives are not sufficiently soluble in aqueous systems.

It has now been found that specific water-soluble derivatives of 2-(2'-hydroxyphenyl)benzotriazoles are readily suitable light stabilising additives for aqueous ink compositions, especially for ink jet printing.

Specifically, the invention relates to aqueous ink compositions which contain, as light stabiliser, at least one compound of formula I (structure I: 2-(2'-hydroxyphenyl)benzotriazole with $R_1$, $R_2$, $R_3$ substituents)

wherein $R_1$ is hydrogen, halogen, $C_1$–$C_4$alkyl, $C_1$–$C_4$alkoxy, —COO—$R_9$—$OSO_3X$, —COOX or —$SO_3X$, $R_2$ is hydrogen, OH, $C_1$–$C_8$alkyl, $C_5$–$C_6$cycloalkyl, phenyl, naphthyl, $C_7$–$C_{12}$aralkyl, halogen, $C_1$–$C_8$alkoxy or a —Y—Z group, $R_3$ is hydrogen, $C_1$–$C_8$alkyl, a —Y—Z group or a —Y—O—Z' group, X is hydrogen or M, M is Li, Na, K, $\frac{1}{2}$ Mg, $\frac{1}{2}$ Ca, $\frac{1}{2}$ Zn, $\frac{1}{2}$ Co (II), $\frac{1}{2}$ Cu (II), $\frac{1}{2}$ Ni (II), $\frac{1}{3}$ Cr (III), $\frac{1}{3}$ Fe (III), (amine structures with $R_4$, $R_5$, $R_6$, $R_7$)

or (piperazine structure with $R_4$, $R_5$, $R_6$, $R_7$)

wherein $R_4$, $R_5$, $R_6$ and $R_7$ are each independently of one another hydrogen, $C_1$–$C_{12}$alkyl, hydroxyethyl, cyclohexyl, phenyl or benzyl, Y is a direct bond or a divalent group of one of the following formulae:

—$R_8$—, —$R_8$—CONH—$R_9$—, —$R_8$—CON($R_{10}$—Z)—$R_9$—,

—CH($COOX$)—$R_8$—, —$R_8$—(phenylene)—, —$R_8$—COO—$R_9$—,

—$R_8$—$SO_2$—$R_9$—, —$R_8$—$SO_2NH$—$R_9$—,

—$R_8$—COO—CH($R_{10}$—Z)—$R_9$— or —$R_8$—COO—G($R_{10}$—Z)($R_{11}$—Z)—$R_9$—, wherein $R_8$, $R_9$, $R_{10}$ and $R_{11}$ are each independently of one another $C_1$–$C_{20}$alkylene which may be substituted by 1–10 hydroxyl groups or are $C_2$–$C_{20}$alkylene which is interrupted by 1–10 —O— or —NH—, and Z is a —COOX or —$SO_3X$ group, and Z' is —$SO_3X$, with the proviso that the compound of formula I contains at least one group of formula —COOX or —$SO_3X$.

$R_1$ as $C_1$–$C_4$alkyl may be methyl, ethyl, propyl, isopropyl, n-butyl, sec-butyl, isobutyl or tert-butyl. $R_2$ and $R_3$ as $C_1$–$C_8$alkyl may further be n-pentyl, sec-pentyl, tert-pentyl, n-hexyl, isohexyl, 2-ethylbutyl, n-heptyl, isoheptyl, n-octyl, 2-ethylhexyl or tert-octyl. $R_4$–$R_7$ as $C_1$–$C_{12}$alkyl may additionally be n-decyl, n-dodecyl or isononyl.

$R_2$ as cycloalkyl or aryl may be cyclopentyl, cyclohexyl, phenyl or naphthyl. $R_2$ as aralkyl may be benzyl, α-methylbenzyl, α,α-dimethylbenzyl or naphthylmethyl.

$R_1$ as $C_1$–$C_4$alkoxy may be methoxy, ethoxy, isopropoxy or butoxy. $R_2$ as $C_1$–$C_8$alkoxy may be additionally pentyloxy, hexyloxy, heptyloxy or octyloxy.

$R_8$ as $C_1$–$C_8$alkylene may be unbranched or branched alkylene, such as methylene, di-, tri-, tetra-, penta-, hexa- and octamethylene, 1,2-propylene or 2-methyltetramethylene. $R_9$, $R_{10}$ and $R_{11}$ as $C_1$–$C_{20}$alkylene may additionally be octa-, deca-, dodeca-, hexadeca- or octadecamethylene. Preferably $R_8$, $R_9$, $R_{10}$ and $R_{11}$ are $C_1$–$C_4$alkylene.

$R_8$, $R_9$, $R_{10}$ and $R_{11}$ as alkylene which is interrupted by —O— may be 3-oxatetramethylene, 3,6-dioxaoctamethylene, 3,6,9,12-tetraoxatetradecamethylene or radicals of formulae —(OC$_2$H$_4$)$_2$— und —(OC$_2$H$_4$)$_6$—. $R_9$, $R_{10}$ and $R_{11}$ as OH-substituted alkylene may be in particular 2-hydroxytrimethylene.

The ink compositions preferably contain, as light stabiliser, a compound of formula I, wherein $R_1$ is hydrogen, halogen, $C_1$–$C_4$alkyl, $C_1$–$C_4$alkoxy, —COO—$R_9$—$OSO_3X$, —COOX or —$SO_3X$, $R_2$ is hydrogen, $C_1$-$C_8$alkyl, $C_7$-$C_9$phenylalkyl or a —Y—Z group, $R_3$ is hydrogen, $C_1$-$C_4$alkyl, —Y—Z group or a —Y—O—Z' group, X is hydrogen or M.

M is Li, Na, K,

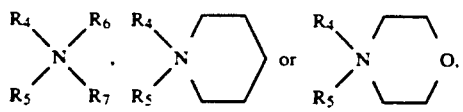

wherein $R_4$, $R_5$, $R_6$ and $R_7$ are each independently of one another H, $C_1$-$C_4$alkyl or hydroxyethyl, Y is a direct bond or a group selected from

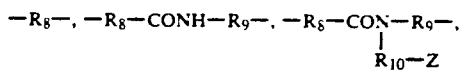

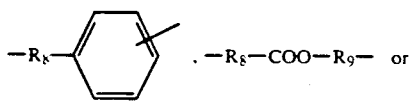

wherein $R_8$ is $C_1$-$C_6$alkylene and $R_9$ and $R_{10}$ are each independently of the other $C_1$-$C_{10}$alkylene which may be substituted by 1 or 2 hydroxyl groups or $C_2$-$C_{20}$alkylene which is interrupted by 1-10 —O—, and Z is a —COOX or —$SO_3X$ group and is Z' —$SO_3X$, especially those compounds of formula I, wherein $R_1$ is hydrogen, chloro, —CO—$OC_2H_4)_x$ $OSO_3X$, —COOX or —$SO_3X$, $R_2$ is hydrogen, $C_1$-$C_8$alkyl, $C_7$-$C_9$phenylalkyl or a —Y—Z group, $R_3$ is hydrogen or a —Y—Z group and x is an integer from 2 to 8.

Particularly preferred ink compositions are those containing a compound of formula I, wherein $R_1$ is hydrogen, chloro, —CO—$OC_2H_4)_x$ $OSO_3X$, —COOX or —$SO_3X$, $R_2$ is hydrogen, $C_1$-$C_8$alkyl, $C_7$-$C_9$phenylalkyl or a —Y—Z group, $R_3$ is hydrogen or a —Y—Z group, x is an integer from 2 to 8, X is Li, Na, K or

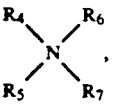

Y is a direct bond or a group selected from —$R_8$—, —$R_8$—CONH—$R_9$—,

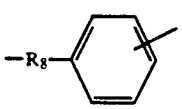

or —$R_8$—COO—$R_9$—,

Z is a —COOX or —$SO_3X$ group, $R_4$, $R_5$, $R_6$ and $R_7$ are each independently of one another $C_1$-$C_4$alkyl or hydroxyethyl, $R_8$ is $C_1$-$C_6$alkylene and $R_9$ is $C_1$-$C_{10}$alkylene which may be substituted by 1 or 2 hydroxyl groups or is $C_2$-$C_{20}$alkylene which is interrupted by 1-10 —O—.

X is preferably Li, Na, K, $NH_4$ or tetraalkylammonium and is most preferably lithium.

The compounds of formula I preferably contain two —COOX or —$SO_3X$ groups, most preferably two —$SO_3X$ groups.

$R_2$ is preferably in ortho-position and $R_3$ is preferably in para-position to the hydroxyl group of the hydroxylphenyl radical in formula I.

Illustrative of individual compounds of formula I are:

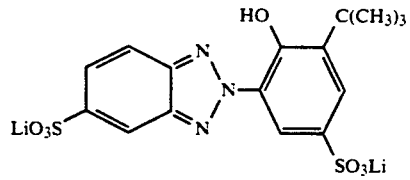

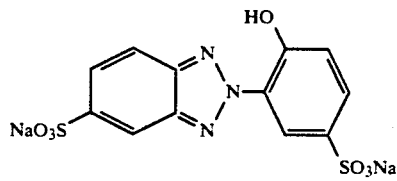

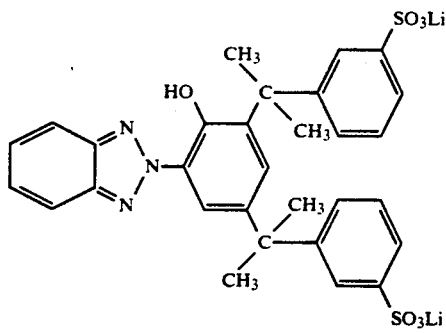

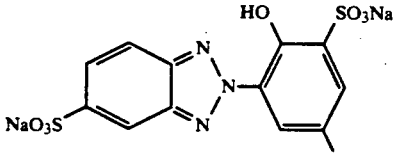

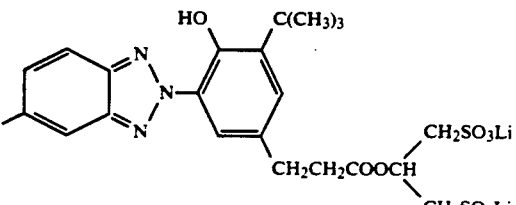

-continued
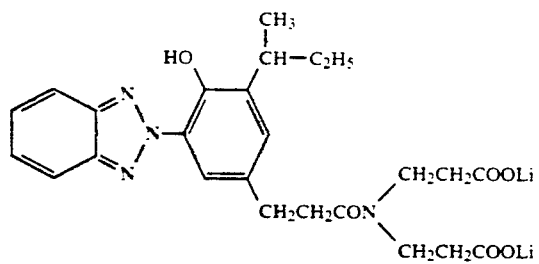
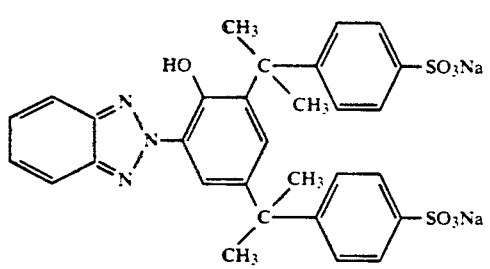
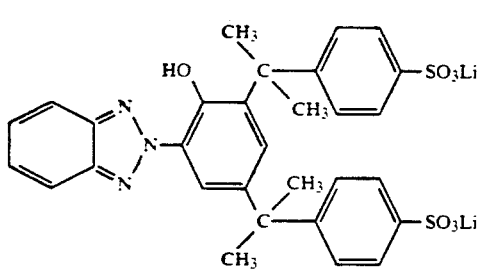
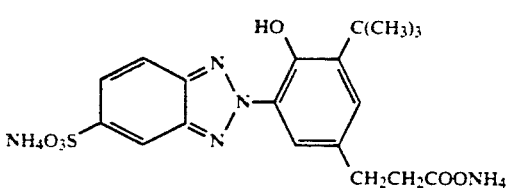
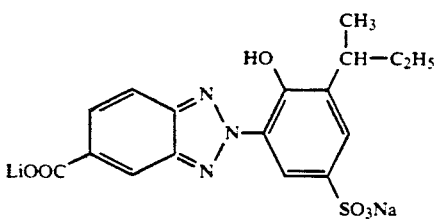
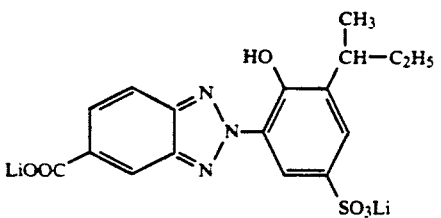
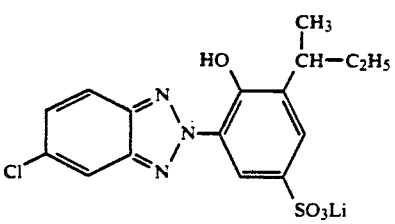
-continued
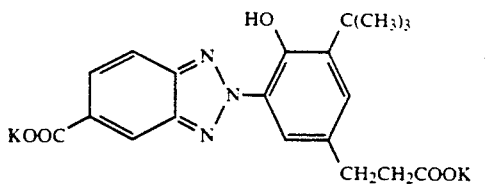
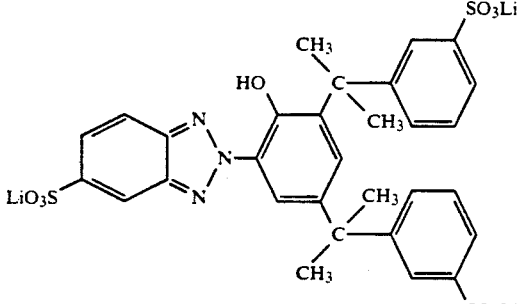
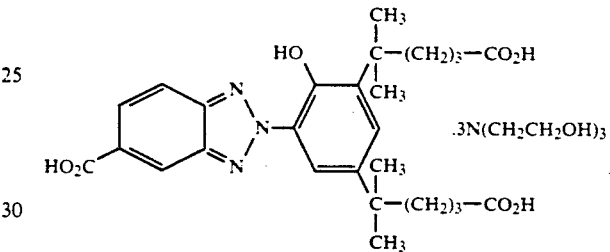
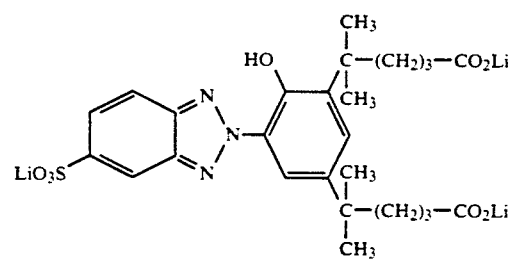
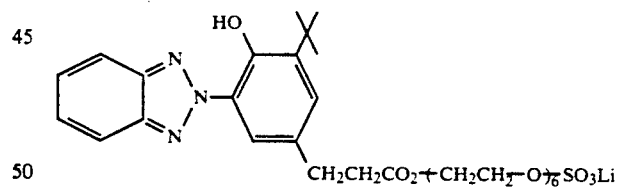
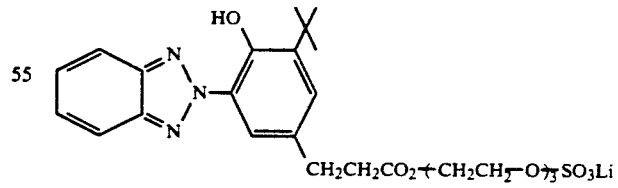
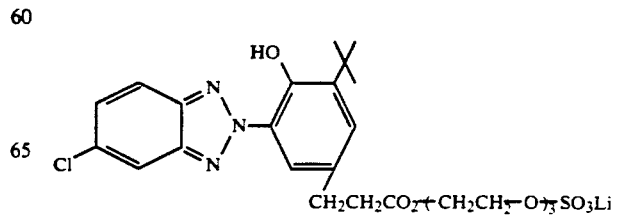

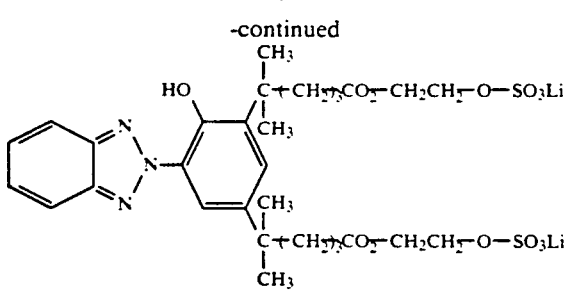

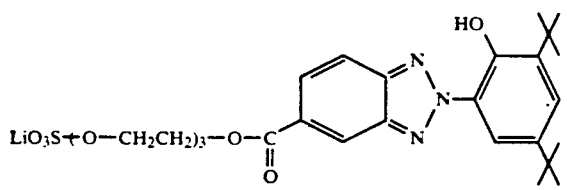

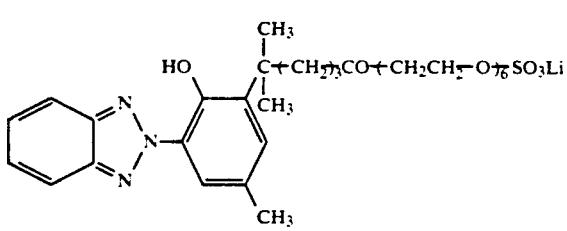

The eligible compounds of the invention contain at least one carboxylic acid or sulfonic acid group or salts thereof. Compounds containing two carboxylic acid groups are already known (GB patent 981 539, French patent 1 370 874). The other compounds are novel compounds and likewise constitute an object of the invention.

Accordingly, the invention also relates to compounds of formula I'

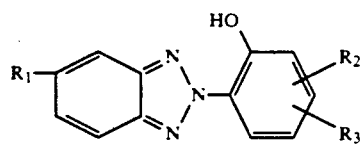

wherein $R_1$ is hydrogen, halogen, $C_1-C_4$alkyl, $C_1-C_4$alkoxy, —COO—$R_9$—OSO$_3$X, —COOM or —SO$_3$X, $R_2$ is hydrogen, OH, $C_1-C_8$alkyl, $C_5-C_6$cycloalkyl, phenyl, naphthyl, $C_7-C_{12}$aralkyl, halogen, $C_1-C_8$alkoxy or a —Y—Z group, $R_3$ is hydrogen, $C_1-C_8$alkyl or a —Y—Z group. X is hydrogen or M.

M is Li, Na, K, ½ Mg, ½ Ca, ½ Zn, ½ Co (II), ½ Cu (II), ½ Ni (II), ⅓ Cr (III), ⅓ Fe (III),

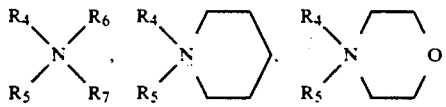

or

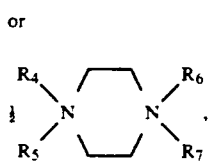

wherein $R_4$, $R_5$, $R_6$ and $R_7$ are each independently of one another hydrogen, $C_1-C_{12}$alkyl, hydroxyethyl, cyclohexyl, phenyl or benzyl, X is hydrogen or M, Y is a group selected from —$R_8$—, —$R_8$—CONH—$R_9$—,

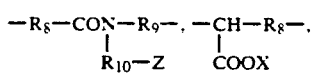

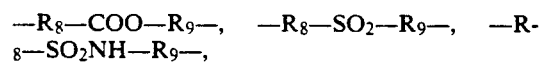

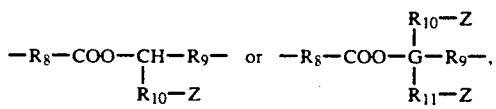

wherein $R_8$, $R_9$, $R_{10}$ and $R_{11}$ are each independently one another $C_1-C_{20}$alkylene which may be substituted by 1-10 hydroxyl groups or $C_2-C_{20}$alkylene which is interrupted by 1-10 —O— or —NH—, and Z is a —COOM or —SO$_3$X group, with the proviso that the compound of formula I' contains at least one —COOX group and/or at least one —SO$_3$X group.

These compounds can be prepared by methods analogous to those for preparing other 2-(2-hydroxyphenyl)-benzotriazoles from the diazonium salts of the corresponding o-nitroanilines by coupling to the corresponding substituted phenols and reduction of the resultant azo compound by cyclisation according to the scheme:

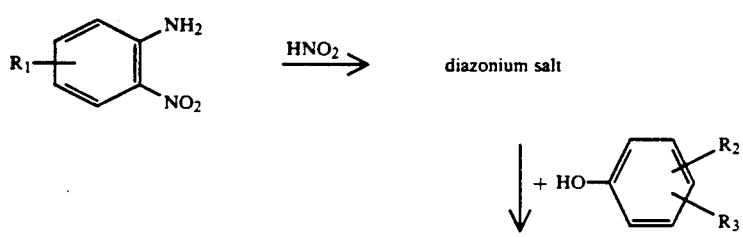

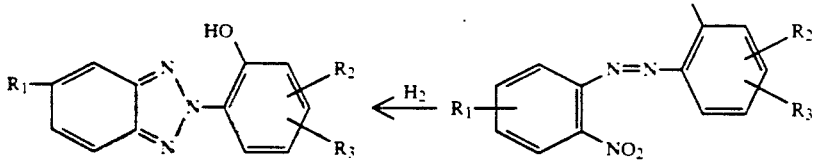

Alternatively, a sulfonic acid radical $R_1$, $R_2$ or $R_3$ can also be introduced by sulfonating the corresponding benzotriazole. The sulfonation can be carried out by the conventional methods of sulfonating aromatic compounds, for example with chlorosulfonic acid. A further alternative method of introducing a sulfonic acid group is the exchange of a tertiary alkyl group $R_2$ or $R_3$ by a $SO_3H$ group by heating in concentrated sulfuric acid.

In these syntheses, the products are normally obtained as the free carboxylic or sulfonic acids, from which the corresponding salts can be prepared by neutralisation with a suitable base, for example by neutralisation with a hydroxide, oxide or carbonate, ammonia or an organic amine.

Those compounds of formula I which contain two —$SO_3X$ groups are preferred.

Also preferred are compounds of formula I', wherein $R_1$ is hydrogen, Cl, —CO—OC$_2$H$_4$)$_x$OSO$_3$X, —COOX or —$SO_3X$, $R_2$ is hydrogen, $C_1$-$C_8$alkyl, $C_7$-$C_9$phenylalkyl or a —Y—Z group, $R_3$ is hydrogen or a —Y—Z group, X is Li, Na, K or

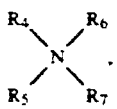

x is an integer from 2 to 8,

Y is a —$R_8$— or —$R_8$—COO—$R_9$—group, wherein $R_8$ and $R_9$ are $C_1$-$C_4$alkylene, and Z is a —COOX or —$SO_3X$ group, with the proviso that the compounds of formula I' contain at least two —$SO_3X$ groups.

In preferred compounds of formula I', the substituent $R_2$ is in ortho-position and the substituent $R_3$ is in para-position to the hydroxyl group of the hydroxyphenyl radical.

The compounds of formula I are preferably added to the ink compositions in an amount of 0.01 to 20% by weight, preferably of 0.1 to 10 % by weight. They are readily soluble in these concentrations.

The ink compositions are aqueous compositions. They contain at least 30% by weight of water. In addition to water, they may contain (up to 70% by weight) one or more water-miscible solvents such as ethylene glycol, di- or triethylene glycol, propylene glycol or ethers of such glycols, 1,4-butanediol, thiodiglycol, glycerol and the ethers thereof, polyglycerol, mono-, di- and triethanolamine, propanolamine, dimethyl formamide, dimethyl sulfoxide, dimethyl acetamide, N-methylpyrrolidone, methanol, ethanol, isopropanol, n-propanol, diacetone alcohol, acetone, methyl ethyl ketone or propylene carbonate.

The ink compositions preferably contain 50% by weight of water.

The ink compositions contain water-soluble dyes or mixtures of the dyes known for colouring natural fibres.

These dyes may be typically mono-, di- or polyazo dyes, triphenylmethane dyes, reactive dyes or phthalocyanine dyes. Examples of such dyes are the dyes Acid Red 14, Acid Red 52, Reactive Red 40, Acid Yellow 17, Acid Yellow 23, Direct Yellow 86, Acid Red 35, Acid Red 249, Direct Red 227, Acid Blue 9, Direct Blue 86, Direct Blue 199, Food Black 2, Direct Black 19, Direct Black 38, Direct Black 168 and Sulphur Black 1 listed in the Colour Index. The ink compositions will normally contain 0.5-6% by weight of dye.

The ink compositions may also contain minor amounts of various modifiers such as binders, surfactants, biocides, corrosion inhibitors, sequestrants, pH buffers or conductivity additives. They may also contain further water-soluble light stabilisers. Normally, however, the addition of one or more stabilisers of formula I to the ink composition will suffice in the practice of this invention.

The stabilised ink compositions of this invention are preferably used for ink jet printing.

They can, however, also be used for all other conventional utilities for inks, for example for felt-tipped pens, ink pads, fountain pens, pen plotters, typewriter ribbons or as printing inks for different printing techniques.

Different techniques are used in ink jet printing, depending on the apparatus employed. Thus, for example, there are drop-on-demand printers, bubble-jet printers, continuous-jet printers or compound-jet printers. The stabilised ink compositions of this invention can be used for all these techniques.

The effect of the addition of a compound of formula I to the ink compositions consists in the enhanced light stability of the printed image produced with the composition. The effect can be measured experimentally by rapid exposure of specimen prints in an exposure apparatus, as shown in the Examples herein. Parts and percentages in these Examples are by weight.

The recording materials of this invention, which are preferably used for ink jet printing, consist of a substrate having a surface which is printable by means of an ink jet. The substrate is normally paper or a plastic sheet and is usually coated on one side with a material which is capable of absorbing ink. This layer will preferably contain $SiO_2$ and polyvinyl alcohol.

Uncoated paper can also be used. In this case, the paper acts simultaneously as substrate and ink absorbing layer. Materials made of cellulosic fibres and textile fibre materials such as cotton fabric or blends of cotton and polyacrylamide or polyester, which materials contain compounds of formula I, can also be used for ink jet printing.

The recording materials can also be tranparent, as in the case of projection transparencies.

Alternatively, the compounds of formula I can also be incorporated into recording materials, particularly those suitable for ink-jet printing.

In the first method, the compounds of the formula I can be added directly to the pulp in the paper manufacture.

A second method of application is spraying the substrate with a solution of compounds of formula I. The solution is in this case an aqueous solution or a solution in a slightly volatile organic solvent. Spraying or impregnating the material with an organic solution of a compound of formula I is especially suitable when using oil-soluble compounds of formula I. The use of emulsions or dispersions is also possible.

Normally, however, a coating composition having affinity for dyes is applied to the substrate and the compounds of formula I are added to this composition. The coating compositions normally consist of a solid filler, a binder and conventional additives.

The filler constitutes the bulk of the coating composition. Examples of suitable fillers are $SiO_2$, kaolin, talcum, calcium, magnesium or aluminium silcates, gypsum, zeolith, bentonite, diatomaceous earth, vermiculite, starch or the surface-modified $SiO_2$ described in JP-A 60-260 377. Minor amounts of white pigments such as titanium dioxide, barytes, magnesium oxide, lime, chalk or magnesium carbonate can be used with the filler in the coating composition, provided they do not drastically lower the density of the ink jet print.

Coating compositions suitable for transparent projectable recording materials may not contain any light-scattering particles such as pigments and fillers.

The binder binds the fillers to one another and to the substrate. Typical conventional binders are water-soluble polymers such as polyvinyl alcohol, partially hydrolysed polyvinyl acetate, cellulose ethers, polyvinyl pyrrolidone and copolymers thereof, polyethylene oxide, salts of polyacrylic acid, sodium alginate, oxidised starch, gelatin, casein, vegetable gum, dextrin, albumin, dispersions and polyacrylates or acrylate/methacrylate copolymers, lattices of natural or synthetic rubber, poly(meth)acrylamide, polyvinyl ethers, polyvinyl esters, copolymers of maleic acid, melamine resins, urea resins or the chemically modified polyvinyl alcohols disclosed in JP-A 61-134 290 or JP-A 61-134 291.

An additional dye receptor or a mordant which enhances the fixation of the dye to the coating may be added to the binder. Dye receptors for acid dyes are cationic or amphoteric. Exemplary of cationic receptors are polymeric ammonium compounds such as polyvinylbenzyltrimethylammonium chloride, polydiallyldimethylammonium chloride, polymethacryloxyethyldimethylhydroxyethylammonium chloride, polyvinylbenzylmethylimidazolium chloride, polyvinylbenzylpicolinium chloride or polyvinylbenzyltributylammonium chloride. Further examples are basic polymers such as poly(dimethylaminoethyl)methacrylate, polyalkylenepolyamines and their condensation products with dicyandiamide, amine/epichlorohydrin polycondensates or the compounds disclosed in JP-A-57-36 692, 57-64 591, 57-187 289, 57-191 084, 58-177 390, 58-208 357, 59-20 696, 59-33 176, 59-96 987, 59-198 188, 60-49 990, 60-71 796, 60-72 785, 60-161 188, 60-187 582, 60-189 481, 60-189 482, 61-14 979, 61-43 593, 61-57 379, 61-57 380, 61-58 788, 61-61 887, 61-63 477, 61-72 581, 61-95 977, 61-134 291 or in U.S. Pat. Nos. 4,547,405 and 4,554,181 as well as in DE-A-3 417 582. An amphoteric dye receptor is, for example, gelatin.

The coating having affinity for dyes may contain a number of other additives such as antioxidants, further light stabilisers (also including UV absorbers which do not conform to the light stabilisers of this invention), viscosity improvers, fluorescent whitening agents, biocides and/or antistatic agents.

Representative examples of particularly suitable antioxidants are sterically hindered phenols and hydroquinones, for example the antioxidants disclosed in GB-A 2 088 777 or JP-A-60-72 785, 60-72 786 and 60-71 796.

Representative examples of particularly suitable light stabilisers are organic nickel compounds and sterically hindered amines, for example the light stabilisers disclosed in JP-A-58-152 072, 61-146 591, 61-163 886, 60-72 785 and 61-146 591 or in GB-A-2 088 777, JP 59-169 883 and 61-177 279.

Suitable UV absorbers which may be added to a coating composition in conjunction with compounds of formula I are disclosed, for example, in Research Disclosure No. 24 239 (1984) page 284, GB-A 2 088 777 and EP-A-0 280 650. Suitable UV absorbers for concurrent use with compounds of formula I in recording substrates for ink jet printing are in particular those of the 2-hydroxyphenylbenzotriazole class and, most particularly, 2-(2'-hydroxy-3',5'-di-t-amylphenyl)benzotriazole and 2-(2'-hydroxy-3'-t-butyl-5'-polyglycolpropionate-phenyl)benzotriazole. The UV absorbers can be added to the coating composition as emulsion or dispersion. If the compound of formula I is an acid, it can be dissolved in the coating composition by addition of alkali. Compounds of formula I which are not acids can be dissolved either direct in the coating composition or are added to it in the form of an emulsion or suspension.

The coating composition is normally applied to the substrate, for example paper, and dried by heating. As already mentioned, the compounds of formula I can be also applied to the recording substrate in a separate operation, alone or together with other already described components, as aqueous solution. Application can be made by spraying, by sizing in a sizing press, by a separate coating operation or by immersion in a vat. After subjecting the recording substrate to such an aftertreatment, an additional drying step is necessary.

The recording substrate preferably contains 1 to 10,000 mg/m$^2$, most preferably 50 bis 2000 mg$^2$, of at least one compound of formula I.

EXAMPLE 1

A coating composition based on silica/polyvinyl alcohol is prepared from the following components:
16.34 g of a 10% solution of polyvinyl alcohol (Riedel de Haen GmbH)
0.02 g of di-tert-octylphenylpolyethylene oxide
2.00 g of silica (Type 244, W.R. Grace and Co.)
9.54 g of water.

The resultant coating composition is dispersed by ultrasonication and filtered through a sieve of polyester fibres having a mesh size of 24 μm. The pH is adjusted to 7.0 by addition of 2N sodium hydroxide solution.

The coating composition is applied with a wire applicator to photographic paper in a thickness of 36 μm. After drying with warm air, the coating has a dry weight of ca. 5.0 g/m$^2$.

The recording material is printed with an ink composition of this invention which contains a UV absorber of formula I and a comparison ink composition which does not contain a UV absorber.

The ink is prepared as follows:
3 g of a UV absorber of formula

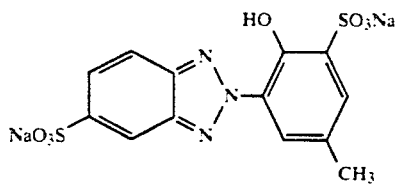

are dissolved in a mixture of 83 g of water and 15 g of glycerol. A dye solution is prepared from 4 g of C.I. Food Black 2 in 80 g of water and 15 g of glycerol. Both solutions are filtered through a membrane filter with a pore size of 0.3 μm. and combined. The printing ink composition so obtained consists of:

81.5% of water
15% of glycerol
2% of dye
1.5% of UV absorber.

The blank specimen is prepared by combining the dye solution with equal parts of a mixture of 86 g of water and 15 g of glycerol.

The inks are filled into ink cartidges of a Hewlett-Packard "Think-Jet" ink jet printer. Specimen prints having a density of 192×96 dots per inch (75.6×37.8 dots per cm$^2$) are prepared.

After storage for 1 week to dry out the print completely, the colour density of the specimen prints is measured with a Macbeth TR 924 densitometer using a status A filter. The specimen prints are then irradiated in an Atlas Weather-O-Meter with a xenon lamp having an intensity of 81 klux behind a filter of 6 mm thick window glass. The colour intensity is measured once more to ascertain the percentage loss of intensity.

The results are reported in the following table. Lower values denote higher lightfastness.

| UV absorber | Loss of colour density after exposure |
|---|---|
| none | 15% |
| 1.5% | 10% |

The same test is made using sodium 2-hydroxy-4-methoxybenzophenone-5-sulfonate as UV absorber. A discolouration of the black print to brownish black occurs.

EXAMPLE 2

An ink concentrate consisting of 4 g of C.I. Acid Red, 25 g of diethylene glycol and 70 g of water, and a UV absorber concentrate consisting of 4 g of UV absorber, 25 g of diethylene glycol and 70 g of water, are prepared. The following compounds are used as UV absorbers:

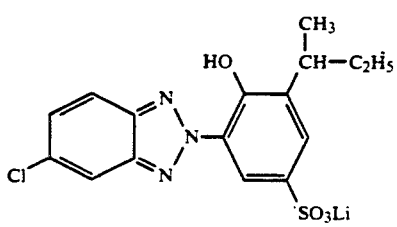

and

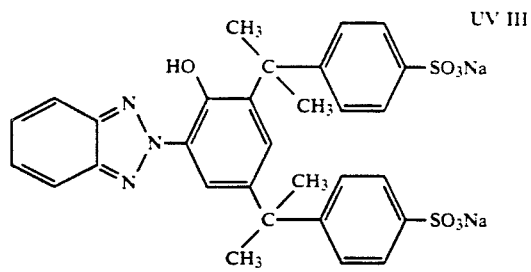

and, as comparision UV absorbers, the compounds of formulae

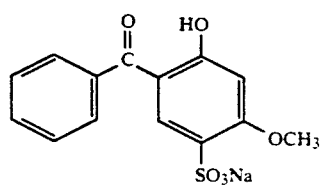

and

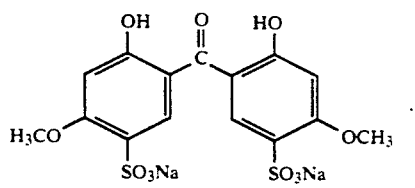

Ink compositions are prepared from 1 part of dye concentrate and UV absorber concentrate and filled into cartridges of a Hewlett Packard Quiet Jet printer. After preparing specimen prints on paper suitable for ink jet printing, the lightfastness of these prints is tested as described in Example 1. The results are reported in Table 1.

TABLE 1

| UV absorber | Loss of density (15 kJ/cm$^2$) |
|---|---|
| without | 63% |
| UV II | 50% |
| UV III | 46% |
| V I | 59% |
| V II | 69% |

EXAMPLE 3

As described in Example 2, ink compositions are prepared from the dyes Food Black 2, Acid Red 14,27,35 and 249, Direct Red 227 and Reactive Red 24, while the UV absorber concentrate consists of 6 g of UV absorber, 25 g of diethylene glycol and 70 g of water.

Prior to use, the concentrate containing Reactive Red is adjusted with lithium hydroxide to pH 12.0, heated for 30 minutes at 95°-100° C., and subsequently adjusted with sulfuric acid to pH 7.

The prints are prepared and the lightfastness test is carried out as described in Example 2. The results are reported in Table 2.

TABLE 2

| UV Absorber | Loss of colour density in % after exposure to light energy of 15 kJ/cm² | | | | | | |
|---|---|---|---|---|---|---|---|
| | Food Black 2 | Acid Red 249 | Direct Red 227 | Acid Red 14 | Acid Red 35 | Reactive Red 24 | Acid Red 27 |
| without | 53 | 63 | 72 | 90 | 75 | 54 | 81 |
| UV I | 35 | 45 | 57 | 78 | 65 | 37 | 63 |
| V I | 47 | 55 | 78 | 85 | 80 | 57 | 78 |
| V II | 57 | 78 | 72 | 91 | 92 | 66 | 88 |

UV I corresponds to the compound of formula

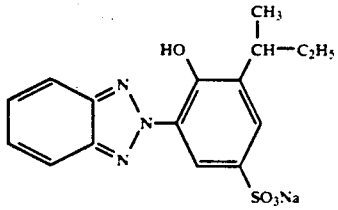

What is claimed is:

1. A method of stabilizing an ink jet print against the deleterious effects of light which comprises
preparing an aqueous solution containing at least 30% by weight of water and
(i) an effective coloring amount of a water soluble dye, and
(ii) 0.01 to 20% by weight, based on the total solution, an effective stabilizing amount, of at least one compound of formula I

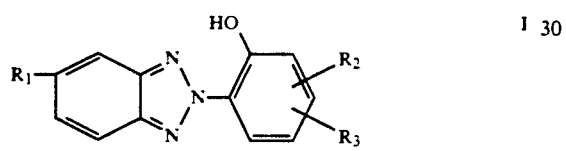

wherein $R_1$ is hydrogen, halogen, $C_1$-$C_4$alkyl, $C_1$-$C_4$alkoxy, —COO—$R_9$—OSO$_3$X, —COOX or —SO$_3$X $R_2$ is hydrogen, OH, $C_1$-$C_8$alkyl, $C_5$-$C_6$-cycloalkyl, phenyl, naphthyl, $C_7$-$C_{12}$aralkyl, halogen, $C_1$-$C_8$alkoxy or a —Y—Z group,
$R_3$ is hydrogen, $C_1$-$C_8$alkyl, a —Y—Z group or a —Y—O—Z' group,
X is hydrogen or M,
M is Li, Na, K, ½ Mg, ½ Ca, ½ Zn, ½ Co (II), ½ Ni (II), ⅓ Cr (III), ⅓ Fe (III),

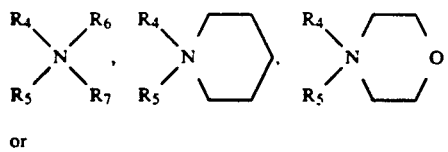

or

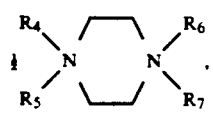

wherein $R_4$, $R_5$, $R_6$ and $R_7$ are each independently of one another hydrogen, $C_1$-$C_{12}$alkyl, hydroxyethyl, cyclohexyl, phenyl or benzyl,
Y is a direct bond or a divalent group of one of the following formulae:

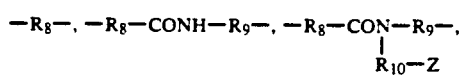

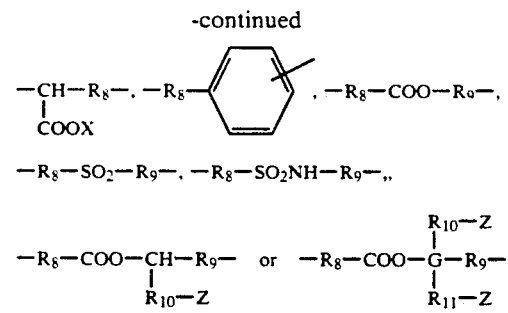

wherein $R_8$, $R_9$, $R_{10}$ and $R_{11}$ are each independently of one another $C_1$-$C_{20}$alkylene which may be substituted by 1-10 hydroxyl groups or are $C_2$-$C_{20}$alkylene which is interrupted by 1-10 —O— or —NH—, and
Z is a —COOX or —SO$_3$X group, and Z' is —SO$_3$X, with the proviso that the compound of formula I contains at least one group of formula —COOX or —SO$_3$X; and then
applying said aqueous solution as an ink onto a recording material for ink jet printing to form an ink jet print containing an effective stabilizing amount of said compound of formula I.

2. A method according to claim 1 where in the compound of formula I
$R_1$ is hydrogen, halogen, $C_1$-$C_4$alkyl, $C_1$-$C_4$alkoxy, —COO—$R_9$—OSO$_3$X, —COOX or —SO$_3$X,
$R_2$ is hydrogen, $C_1$-$C_8$alkyl, $C_7$-$C_9$phenylalkyl or a —Y—Z group,
$R_3$ is hydrogen, $C_1$-$C_4$alkyl, —Y—Z group or a —Y—O—Z' group,
X is hydrogen or M,
M is Li, Na, K,

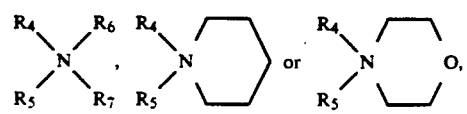

wherein $R_4$, $R_5$, $R_6$ and $R_7$ are each independently of one another H, $C_1$-$C_4$alkyl or hydroxyethyl,
Y is a direct bond or a group selected from —$R_8$—, —$R_8$—CONH—$R_9$—,

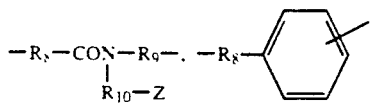

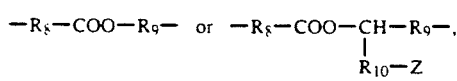

wherein $R_8$ is $C_1$-$C_6$alkylene and $R_9$ and $R_{10}$ are each independently of the other $C_1$-$C_{10}$alkylene which may be substituted by 1 or 2 hydroxyl groups or $C_2$-$C_{20}$alkylene which is interrupted by 1-10 —O—, and Z is a —COOX or —SO$_3$X group and is Z' —SO$_3$X.

3. A method according to claim 2 where in the compound of formula I $R_1$ is hydrogen, chloro, —CO—OC$_2$H$_4$)$_x$ OSO$_3$X, —Y—Z group, $R_3$ is hydrogen or a —Y—Z group and x is an integer from 2 to 8, and M, X, Y and Z are as defined in claim 2.

4. A method according to claim 3 where in the compound of formula I, $R_1$, $R_2$ and $R_3$ are as defined in claim 3, X is Li, Na, K or

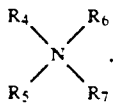

Y is a direct bond or a group selected from —R$_8$—, —R$_8$—CONH—R$_9$—,

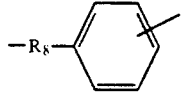

or —R$_8$—COO—R$_9$—,

Z is a —COOX or —SO$_3$X group, and $R_4$, $R_5$, $R_6$ and $R_7$ are each independently of one another H, $C_1$-$C_4$alkyl or hydroxyethyl, $R_8$ is $C_1$-$C_6$alkylene and $R_9$ is $C_1$-$C_{10}$alkylene which may be substituted by 1 or 2 hydroxyl groups or $C_2$-$C_{20}$alkylene which is interrupted by 1-10 —O—.

5. A method according to claim 1 where in the compound of formula I, $R_2$ is in the ortho-position and $R_3$ is in the para-position to the OH group.

6. A method according to claim 1 wherein component (ii) is 0.1 to 10% by weight based on the total solution.

7. A method according to claim 1 wherein the compound of formula I is

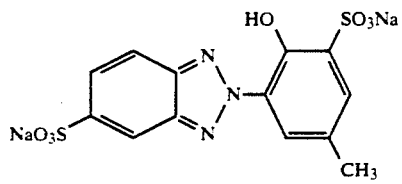

8. A method according to claim 1 wherein the compound of formula I is

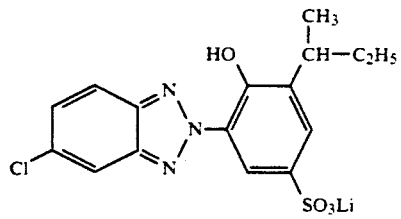

9. A method according to claim 1 wherein the compound of formula I is

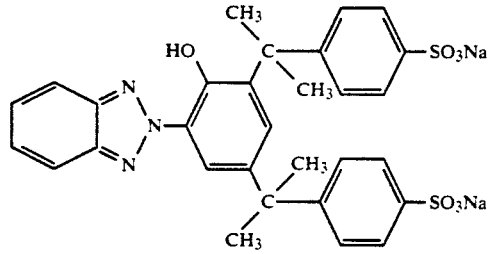

* * * * *